(12) United States Patent
Hidaka

(10) Patent No.: US 11,253,404 B2
(45) Date of Patent: Feb. 22, 2022

(54) APPARATUS FOR APPLYING ADHESIVE TO STRETCHABLE MEMBERS AND STRETCHABLE COMPOSITE SHEET

(71) Applicant: Sun Tool Corporation, Moriguchi (JP)

(72) Inventor: Shoji Hidaka, Moriguchi (JP)

(73) Assignee: SUN TOOL CORPORATION, Moriguchi (JP)

( * ) Notice: Subject to any disclaimer, the term of this patent is extended or adjusted under 35 U.S.C. 154(b) by 388 days.

(21) Appl. No.: 16/341,649

(22) PCT Filed: Oct. 12, 2017

(86) PCT No.: PCT/JP2017/038094
§ 371 (c)(1),
(2) Date: Apr. 12, 2019

(87) PCT Pub. No.: WO2018/070547
PCT Pub. Date: Apr. 19, 2018

(65) Prior Publication Data
US 2019/0365576 A1    Dec. 5, 2019

(30) Foreign Application Priority Data
Oct. 14, 2016  (JP) .............................. JP2016-214678

(51) Int. Cl.
*A61F 13/49*      (2006.01)
*A61F 13/15*      (2006.01)
(Continued)

(52) U.S. Cl.
CPC .... *A61F 13/4902* (2013.01); *A61F 13/15739* (2013.01); *A61F 13/15747* (2013.01);
(Continued)

(58) Field of Classification Search
CPC .......... A61F 13/15747; A61F 13/15593; A61F 2013/49025; B05C 5/0241
See application file for complete search history.

(56) References Cited

U.S. PATENT DOCUMENTS 2,979,577 A * 4/1961 Adler ....................... H01H 1/62
                                                    200/19.28
2004/0158217 A1* 8/2004 Wu ................... A61F 13/15723
                                                    604/385.01

FOREIGN PATENT DOCUMENTS

JP        2518953 Y2    12/1996
JP        11-104173 A    4/1999
(Continued)

OTHER PUBLICATIONS

International Search Report dated Jan. 9, 2018 of corresponding International Application No. PCT/JP2017/038094.

*Primary Examiner* — Mark A Osele
*Assistant Examiner* — Christopher C Caillouet
(74) *Attorney, Agent, or Firm* — Norton Rose Fulbright US LLP

(57) ABSTRACT

A stretchable composite sheet, wherein pleat-free regions where no pleats are formed are formed between a plurality of pleat formation regions, the sheet being made by a method, wherein non-continuous coating sections are set so as to correspond to form the plurality of pleat formation regions, and non-coating sections are set so as to correspond to form the pleat-free regions, and an intermittent coating is performed on stretchable elastic members (rubber threads). An apparatus for non-continuously and intermittently applying a hot-melt adhesive comprises an intermittent coating unit, which includes a hot-melt supply control device having a valve mechanism and a coating head having slit grooves in which coating areas are formed, and a non-continuous coating unit, which vertically vibrates rubber threads, pass- (Continued)

ing through the coating areas, between a coating position and a non-coating position.

3 Claims, 17 Drawing Sheets

(51) Int. Cl.
  *B05C 5/02* (2006.01)
  *B05C 11/00* (2006.01)
(52) U.S. Cl.
  CPC ............... *B05C 5/02* (2013.01); *B05C 11/00* (2013.01); *A61F 2013/1591* (2013.01); *A61F 2013/49025* (2013.01)

(56) References Cited

FOREIGN PATENT DOCUMENTS

| | | |
|---|---|---|
| JP | 2001-347209 A | 12/2001 |
| JP | 2002-653 A | 1/2002 |
| JP | 2003-285004 A | 10/2003 |
| JP | 2009-90274 A | 4/2009 |
| JP | 5997404 B1 | 9/2016 |
| WO | 2006118355 A1 | 11/2006 |

* cited by examiner

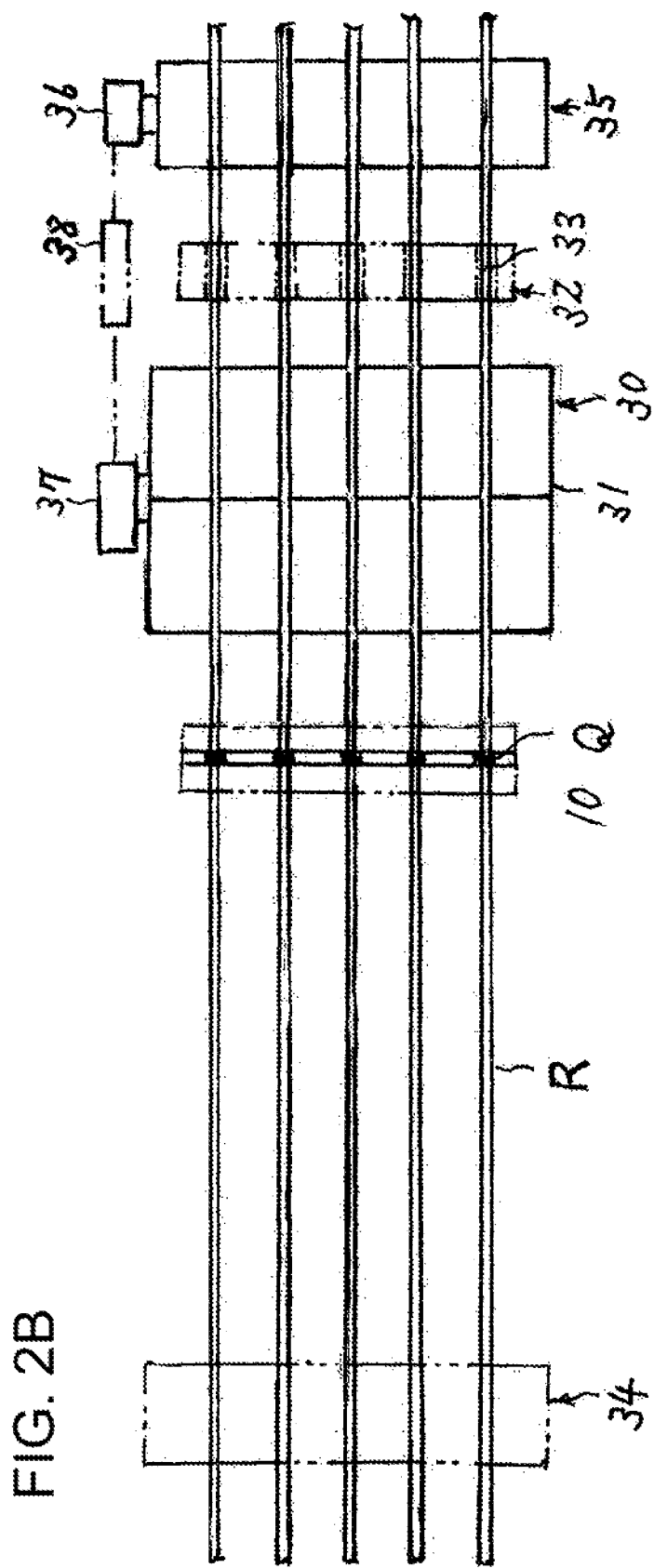

APPARATUS FOR APPLYING ADHESIVE TO STRETCHABLE MEMBERS AND STRETCHABLE COMPOSITE SHEET

CROSS REFERENCE TO RELATED APPLICATIONS

This application is a national stage application pursuant to 35 U.S.C. § 371 of International Application No. PCT/JP2017/38094, filed on Oct. 12, 2017 which claims priority under 35 U.S.C. § 119 to Japanese Patent Application No. 2016-214678 filed on Oct. 14, 2016, the disclosures of which are hereby incorporated by reference in their entireties.

TECHNICAL FIELD

The present invention relates to a composite stretchable member that is flexible, has a pleasant feel, and is capable of forming gathers that are soft to the touch, and, as an apparatus for manufacturing this stretchable member, to an apparatus for applying an adhesive to stretchable members (rubber threads).

BACKGROUND ART

In absorbent products such as disposable diapers and sanitary napkins, it is common practice to join elastic members in a stretched state to a sheet material, and then allow the elastic members to contract to form gathers or pleats (stretchable portions having numerous folds) in the sheet material.

In Patent Literature 1 (see FIG. 16) describes a disposable diaper comprising an elastic stretchable component, which is an elastic stretchable component having a sheet material F made of nonwoven fabric and elastic members sandwiched between a two-layer portion formed by folding back this sheet material, wherein linear joining portions HM' of the sheet material extending perpendicular to the stretch direction of these elastic members are formed, and the elastic members R are joined to the sheet material at these joining portions.

Patent Literature 2 discloses an absorbent product having side flaps 105 on both sides (see FIG. 17). The side flaps 105 are made up of a plurality of pleats 112, and grooves 115 are formed between the pleats with flat surfaces presenting between the pleats 112.

Patent Documents

Patent Literature 1: Japanese Utility Model Registration No. 2518953
Patent Literature 2: Japanese Patent Application Laid-Open (Kokai) No. H11-104173

Problems to be Solved by the Invention

In the elastic stretchable component described in Patent Literature 1, the sheet bulges out between linear joining portions to form uniform pleats; however, because of these linear joining portions, flexibility is poor in the direction parallel to the joining portions; as a result, a problem is that the product is neither soft nor pleasant to the touch.

In other words, an adhesive is applied to two sheets to form linear application areas, and one side of each of a plurality of elastic members (rubber threads) is bonded to the linear application areas, thereby fixing the sheets together, and the two sheets and the rubber threads are also fixed to each other; accordingly, the existence of these linear application areas causes problems when used in a product such as a pleated diaper.

It is an object of the present invention to solve the above problems and to form non-pleated sections between pleated sections. It is another object of the present invention to make a plurality of pleats continuous by forming flat surfaces between the individual pleats, so that it makes easier to produce a product in which flat surfaces are formed between pleats and the plurality of pleats are continuous.

Means for Solving the Problems

The first aspect of the invention
provides an apparatus for applying an adhesive to stretchable members, comprising a coating head that has slit grooves in which coating agent reservoirs are formed and that applies an adhesive over the entire peripheral surface of rubber threads passing through the coating agent reservoirs, and a rubber thread vertical drive device that moves the rubber threads passing through the coating agent reservoirs up and down between a coating position at which the rubber threads pass through the coating agent reservoirs and a non-coating position at which the rubber threads pass away from the coating agent reservoirs.

The second aspect of the invention
provides an apparatus for applying an adhesive to stretchable members, comprising a coating head that has slit grooves in which coating agent reservoirs are formed and that applies an adhesive over the entire peripheral surface of rubber threads passing through the coating agent reservoirs, and a rubber thread vertical drive device that moves the rubber threads passing through the coating agent reservoirs up and down between a coating position at which the rubber threads pass through the coating agent reservoirs and a non-coating position at which the rubber threads pass away from the coating agent reservoirs,
wherein the rubber thread vertical drive device is a rotating cam body that has a plurality of protrusions around its peripheral surface and is driven synchronously with the feeding speed of the rubber threads.

The third aspect of the invention
provides the apparatus for applying an adhesive to stretchable members according to the second aspect of the invention, wherein the rotating cam body constituting the rubber thread vertical drive device has a plurality of protrusions on part of its peripheral surface, and at least one pleat is formed by one rotation of the rotating cam body.

The fourth aspect of the invention
provides the apparatus for applying an adhesive to stretchable members according to the second aspect of the invention, wherein the rotating cam body constituting the rubber thread vertical drive device has a plurality of continuous two protrusions on part of its peripheral surface, with protrusion sections and flat sections being formed alternately, and at least one pleat and at least one flat part are formed by one rotation of the rotating cam body.

The fifth aspect of the invention
provides a stretchable composite sheet in which a plurality of stretchable elastic members (rubber threads) are bonded and fixed between two nonwoven fabric sheets to form two-layer pleats (gathers) orthogonal to the plurality of stretchable elastic members (rubber threads), wherein
the pleats are formed such that both sides of the plurality of stretchable elastic members (rubber threads) are bonded and fixed to the nonwoven fabrics at contact points between the peaks of the two-layer pleats (gathers) and the plurality of stretchable elastic members (rubber threads) that are positioned orthogonally to the peaks of the pleats (gathers), and thus a plurality of pleat formation regions are formed, and between the plurality of pleat formation regions, pleat-free regions where no pleats are formed are formed.

Effects of the Invention

In the composite elastic sheet of the present invention, the joining portions between the rubber threads and the nonwoven fabric are point contacts; as a result, the product is more flexible and feels better than sheets having linear joints, the pleats (stretchable portions having numerous folds) are soft to the touch, and such pleats can be formed in absorbent products and the like, having the effect of reducing amount of adhesive used.

Further, although the joining portions are point contacts, the rubber threads are bonded and fixed on its both sides (top and bottom) to the nonwoven fabrics, an effect to securely join the two sheets of nonwoven fabric and the rubber threads is provided.

Furthermore, because pleat-free regions where there are no pleats are formed between a plurality of pleat formation regions, an effect thereof is that it is possible to provide a stretchable composite sheet that is suitable for various applications as an intermediate product for manufacturing products for absorption of bodily fluids, such as a disposable diapers.

BRIEF DESCRIPTION OF THE DRAWINGS

FIG. 1A and FIG. 1B are overviews of an apparatus for applying an adhesive to a stretchable member according to a first aspect of the invention of the present application, wherein FIG. 1A is a front view thereof, and FIG. 1B is a top view thereof.

FIG. 2A and FIG. 2B are overviews of an apparatus for applying an adhesive to a stretchable member according to a second aspect of the invention of the present application, wherein FIG. 2A is a front view thereof, and FIG. 2B is a top view thereof.

FIG. 3A and FIG. 3B are overviews of an apparatus for applying an adhesive to a stretchable member according to a third aspect of the invention of the present application, wherein FIG. 3A is a front view thereof, and FIG. 3B is a top view thereof.

FIG. 4A and FIG. 4B are overviews of an apparatus for applying an adhesive to a stretchable member according to a fourth aspect of the invention of the present application, wherein FIG. 4A is a front view thereof, and FIG. 4B is a top view thereof.

FIG. 11A and FIG. 11B are illustrations of a stretchable elastic member (rubber thread) in an extended state and on which a non-continuous adhesive application has been made, wherein FIG. 11A is a top view thereof, and FIG. 11B is a detail vertical cross sectional view thereof at an adhesive application position.

FIG. 12A and FIG. 12B are illustrations of a stretchable composite sheet in a state in which a nonwoven fabric is integrated above and below stretchable elastic members (rubber threads) which are in an extended state and on which a non-continuous adhesive application has been made, wherein FIG. 12A is a top view thereof, and FIG. 12B is an enlarged vertical cross sectional view thereof.

FIG. 14A and FIG. 14B are illustrations of a stretchable composite sheet in an extended state, wherein FIG. 14A is a top view thereof, and FIG. 14B is an enlarged vertical cross sectional view thereof.

BEST MODE FOR CARRYING OUT THE INVENTION

Figure 1A:
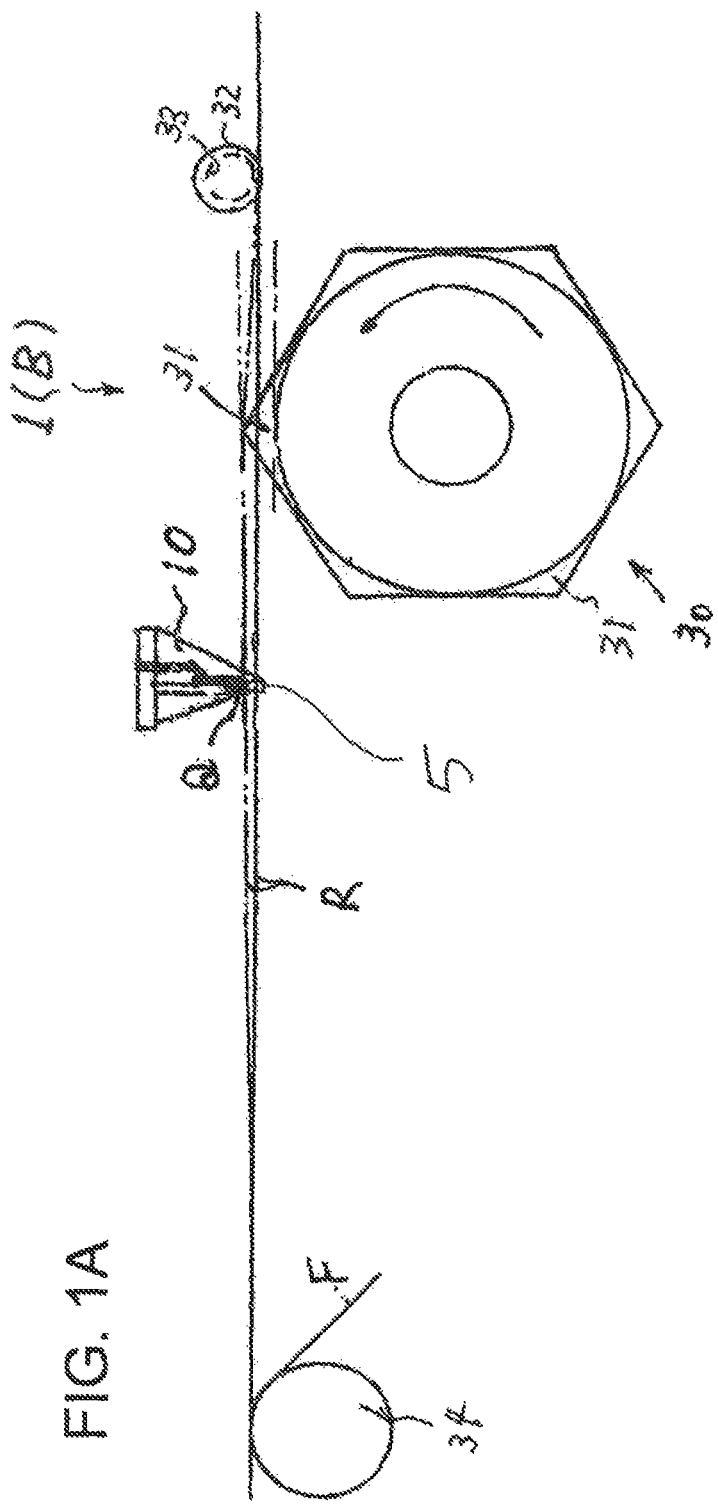
Figure 1B:
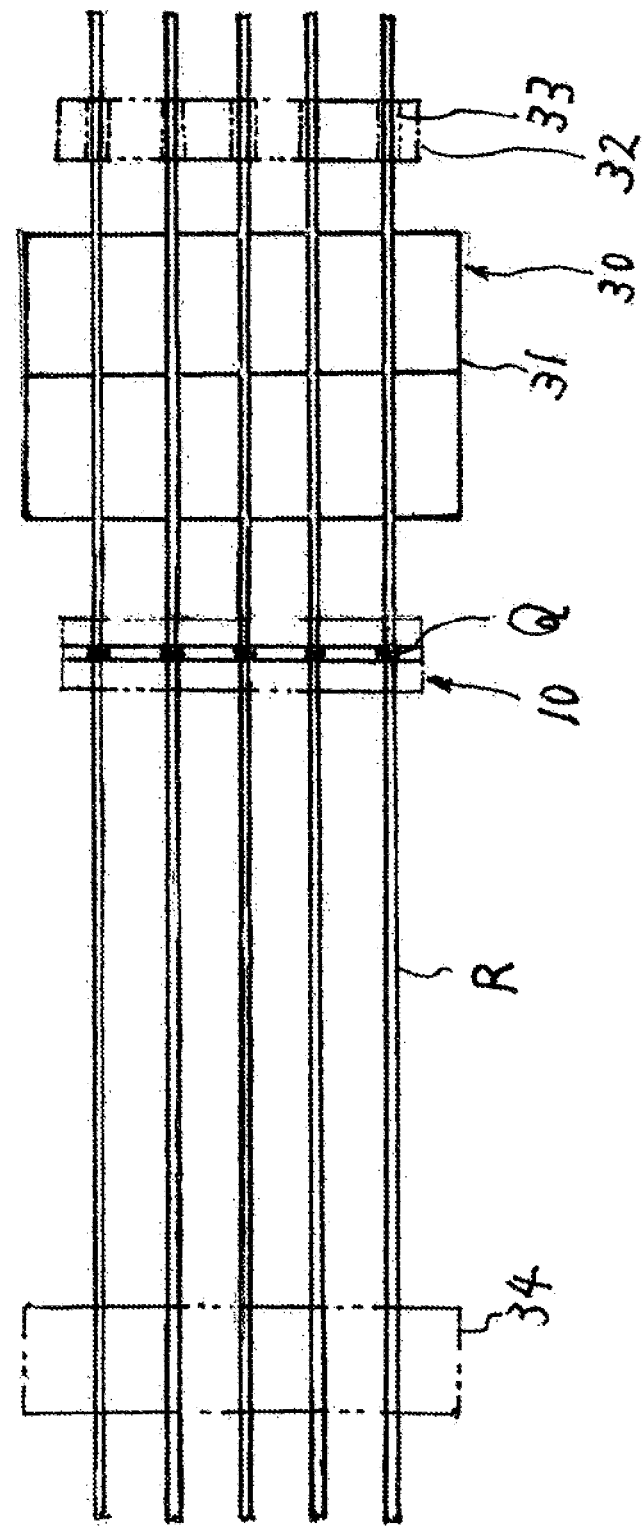

An apparatus for applying an adhesive to a stretchable member according to the first aspect of the invention of the present application will now be described with reference to FIG. 1A and FIG. 1B. This apparatus is comprised of:

a coating head 10 that has slit grooves 5 in which coating agent reservoirs Q are formed and that applies an adhesive HM over the entire peripheral surface of stretchable members (rubber threads) R passing through the coating agent reservoirs Q, and a stretchable member (rubber thread) vertical drive device 1 that moves the rubber threads R passing through the coating agent reservoirs of the slit grooves up and down between a coating position (FIG. 5) at which the rubber threads pass through the coating agent reservoirs and a non-coating position (FIG. 6) at which the rubber threads pass away from the coating agent reservoirs Q.

The rubber thread vertical drive device 1 is constituted by a rotating cam body 30 that has a plurality of protrusions 31 on its peripheral surface. A guide roller 32 having guide grooves 33 for feeding the stretchable members (rubber threads) R is provided, and a drive roller 34 for feeding a nonwoven fabric F is provided on the downstream side of the feeding.

Figure 2A:
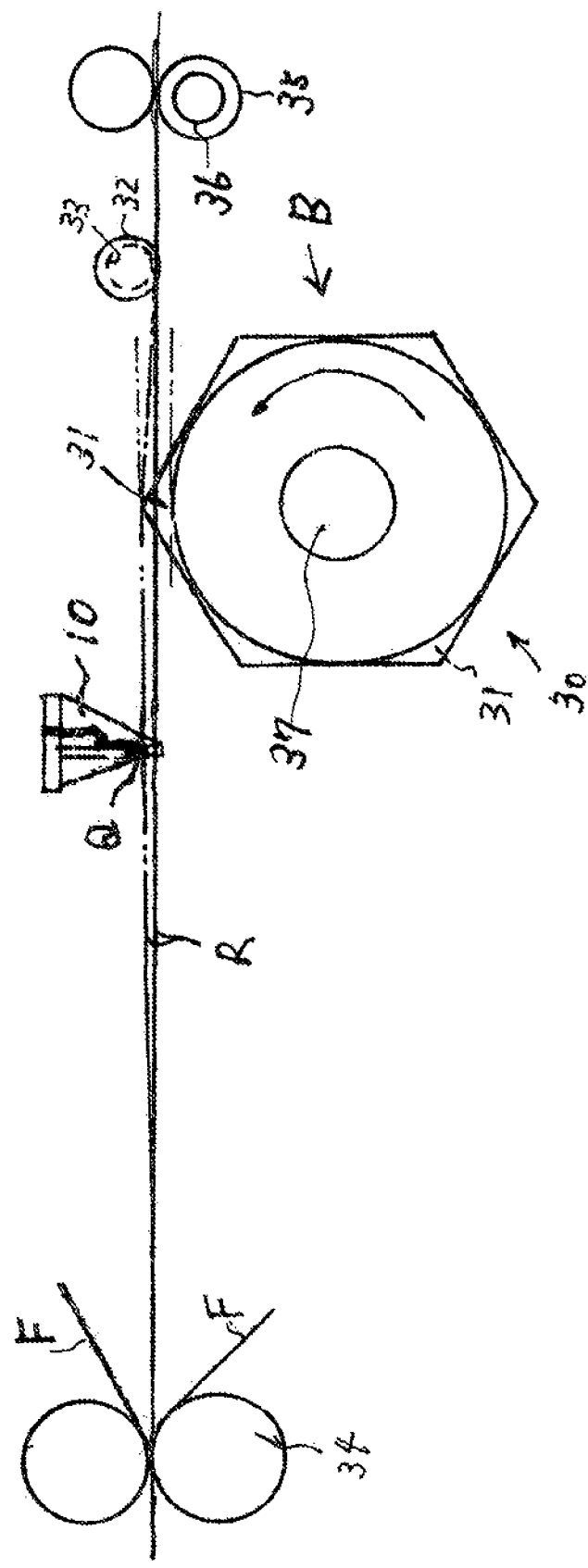

An apparatus for applying an adhesive to a stretchable member according to the second aspect of the invention of the present application will now be described with reference to FIG. 2A and FIG. 2B. As in FIG. 1A and FIG. 1B, the rubber thread vertical drive device is constituted by a rotating cam body 30 that has a plurality of protrusions 31 on its peripheral surface.

Also provided are a drive motor 36 for a drive roller 35 for feeding the stretchable members (rubber threads) R, and a servo control mechanism 38 for a drive motor 37 for the rotating cam body 30, so that the feeding speed of the rubber threads and rotational speed of the rotating cam body 30 are synchronized.

An apparatus for applying an adhesive to a stretchable member according to the third aspect of the invention of the present application will now be described with reference to FIG. 3A and FIG. 3B. A plurality of protrusions 31 are formed adjacently on part of the peripheral surface of the rotating cam body 30 that constitutes a rubber thread vertical drive device B.

Figure 3A:
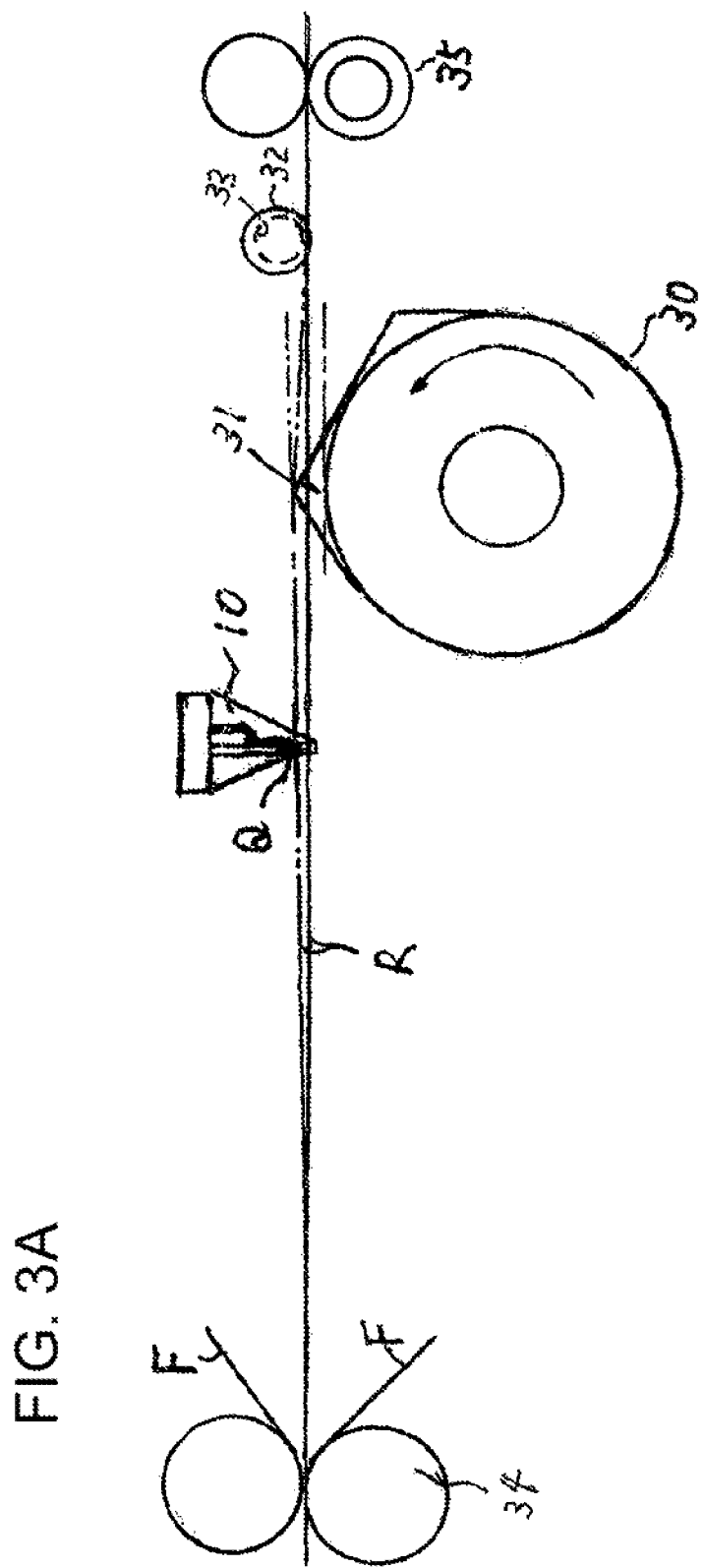
Figure 3B:
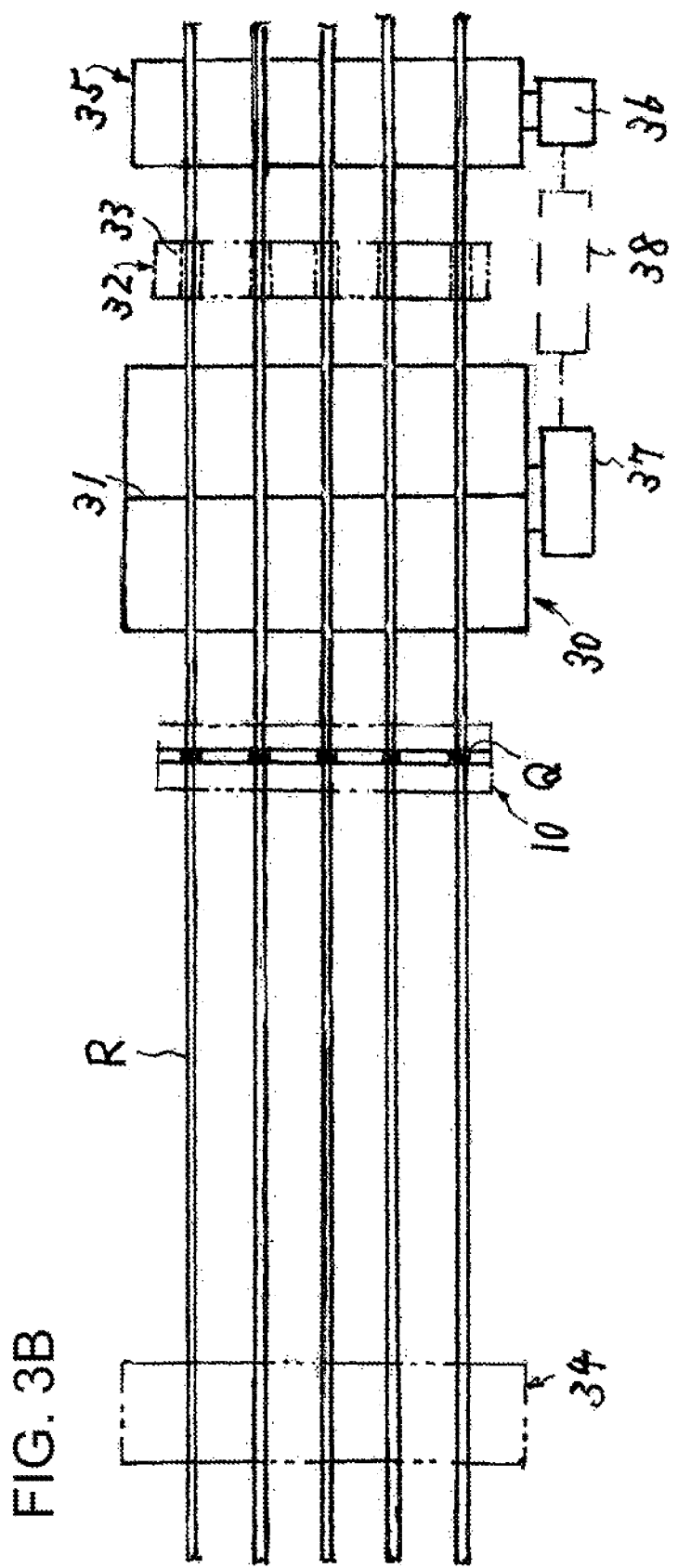

In the embodiment shown in FIG. 3A and FIG. 3B, the protrusions 31 are adjacent to each other over a range of 2/6 of the entire peripheral surface of the rotating cam body 30, and they are not provided over the rest of the peripheral surface range, resulting in that at least one pleat is formed by one rotation of the rotating cam body 30.

Figure 4A:
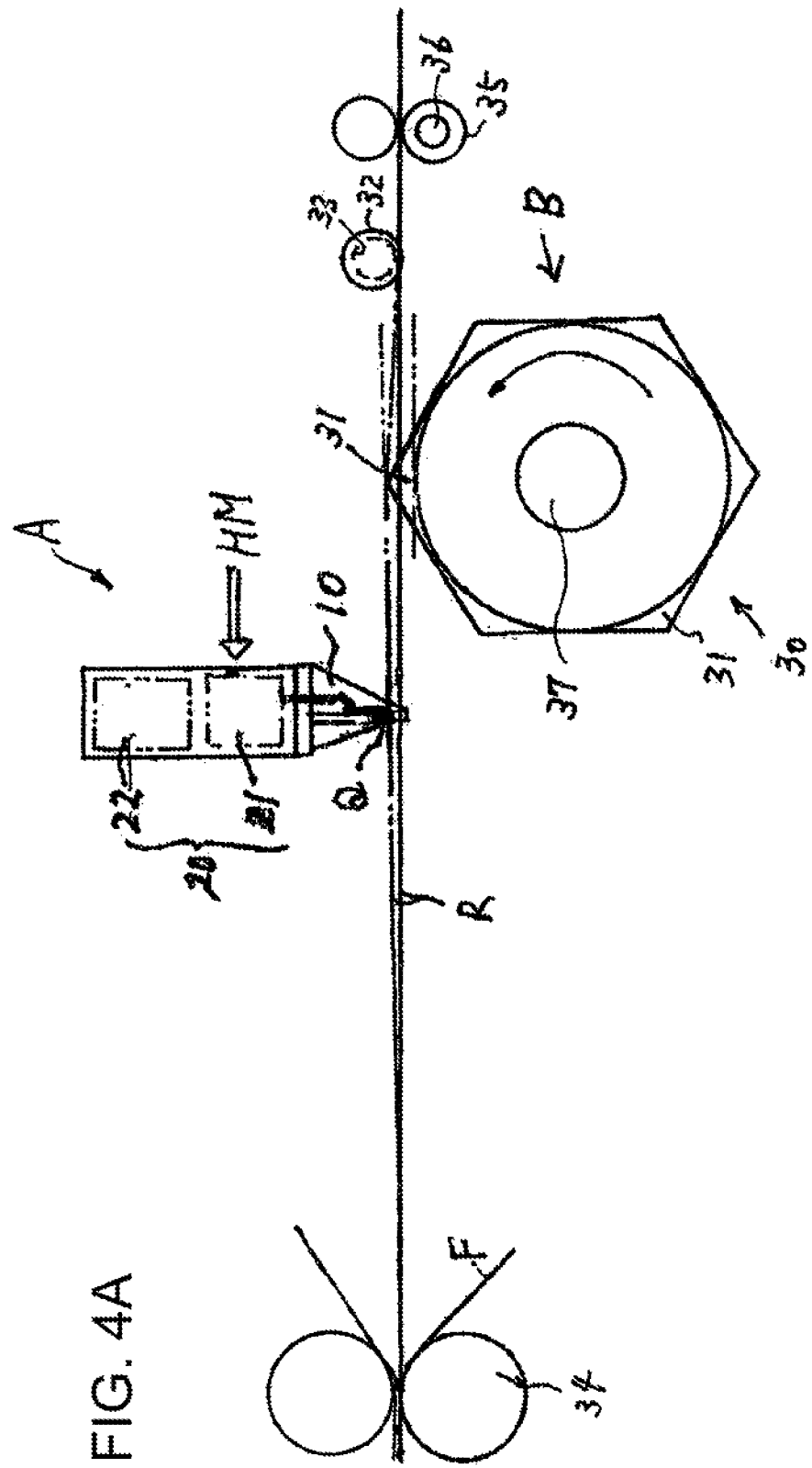
Figure 4B:
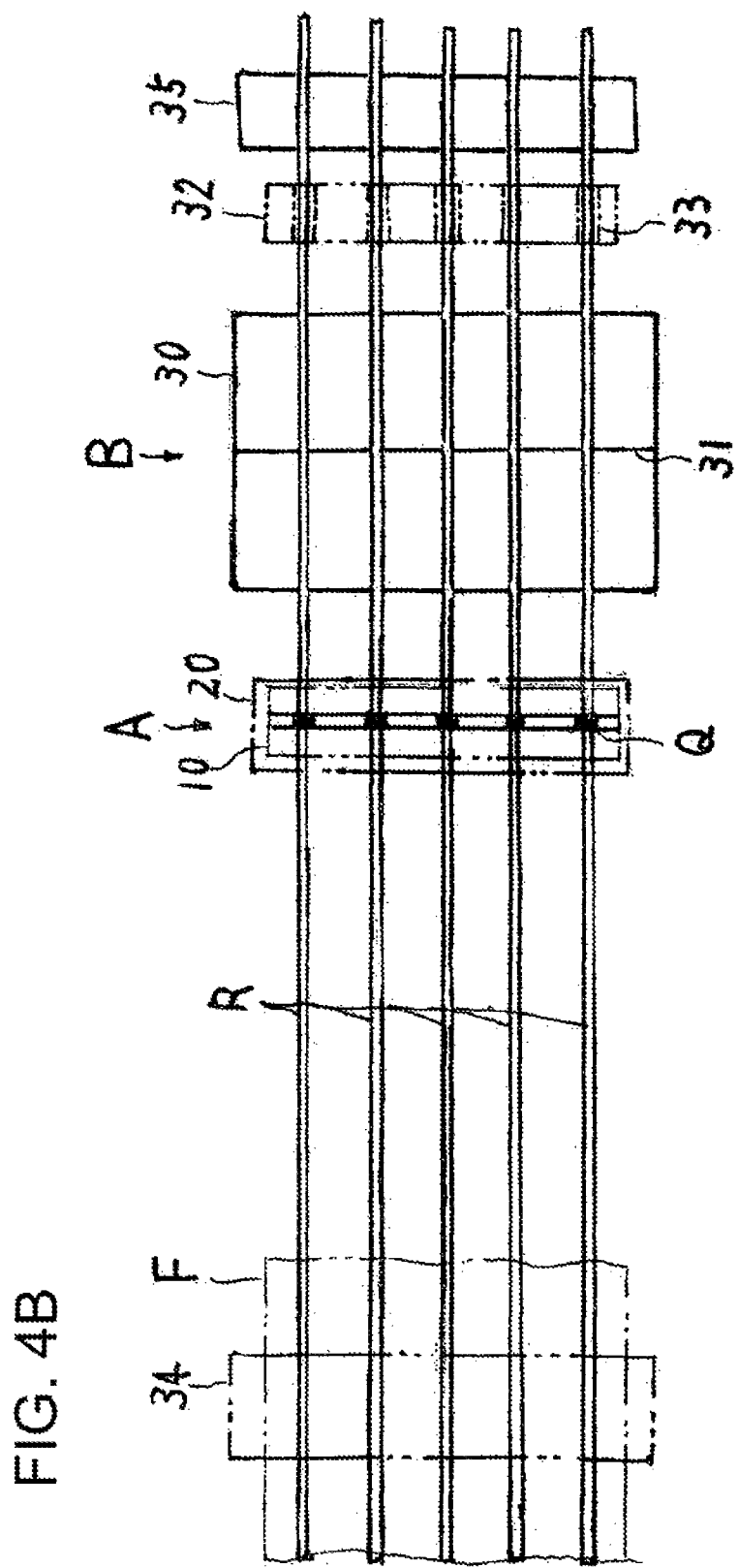

An apparatus for applying an adhesive to a stretchable member according to the fourth aspect of the invention of the present application will now be described with reference to FIG. 4A and FIG. 4B. A characteristic feature thereof is that an intermittent coating is performed to form coating sections TT and non-coating sections NN, and the apparatus is comprised of an intermittent coating unit A and a non-continuous coating unit B.

The intermittent coating unit A is constituted by a coating head 10 and a hot-melt supply control device 20 that has a valve mechanism 21 and a valve drive mechanism 22.

The non-continuous coating unit B has a mechanism to vertically vibrate the protrusions 31 that come into contact with the traveling rubber threads, and causes the rubber threads traveling through the coating area of the coating head 10 to vibrate up and down between a coating position and a non-coating position, so that the traveling rubber threads are rapidly moved between a position where they pass through the coating area of the coating head and a position where they are moved away from the coating area, thus performing a non-continuous coating to the rubber threads.

In the shown embodiment, the non-continuous coating unit B is configured such that protrusions 31 project out from the periphery of a cylindrical body, forming a hexagonal prism-shaped rotating body 30 in a horizontal arrangement. Thus, this non-continuous coating unit B corresponds to the stretchable member (rubber thread) vertical drive device 1 in the embodiments of FIG. 1A to FIG. 3B described above.

In this embodiment, the protrusions 31 stick out around the periphery of the cylindrical body, so that the hexagonal prism-shaped rotating body 30 is provided in a horizontal arrangement.

The non-continuous coating unit B is positioned in front of the intermittent coating unit A, and it produces a non-continuous coating operation in the coating section TT of the intermittent coating unit A, and it substantially does not operate in the non-coating section NN.

The non-continuous coating operation of the stretchable member (rubber thread) vertical drive device 1 (non-continuous coating unit B) will now be described.

Figure 5:
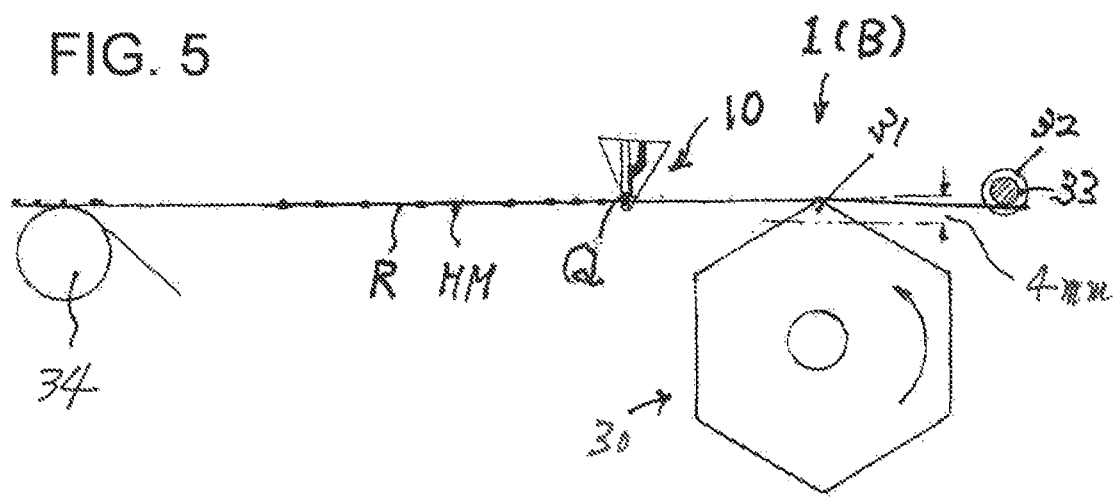
FIG. 5 is a diagram illustrating an operation of coating timing of the present invention, in a front view similar to FIG. 1A.

In FIG. 5, 32 is a guide roller, and 33 is a guide face of the guide roller. 34 is a drive roller. The positions of the rubber threads R are restricted between the guide face 33 of the guide barrel and the drive roller 34.

At the coating timing shown in FIG. 5, the protrusion 31 of the rotating body 30 comes into contact with the rubber threads R and pushes them upward to an upper position.

In this state, the rubber threads R are passing through the coating area Q of the coating head 10. This is a coating state.

Figure 6:
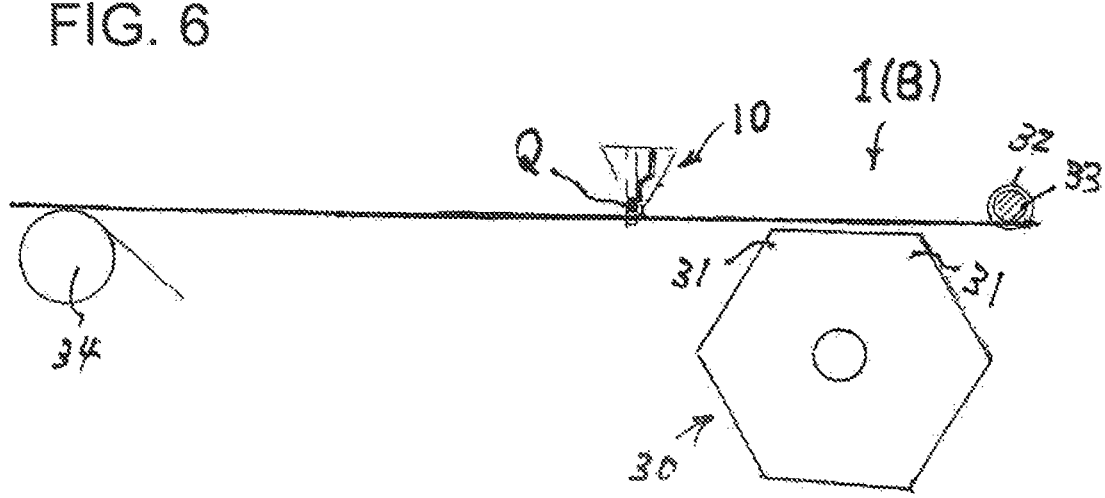
FIG. 6 is a front view showing likewise the non-coating timing.
Figure 7:
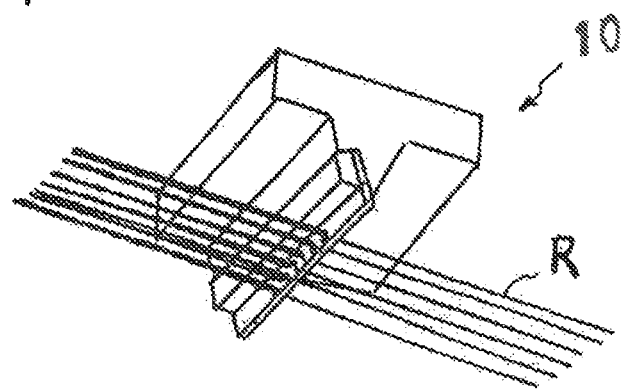
FIG. 7 is a perspective view of a coating head which is an example of a means for applying an adhesive to rubber threads.
Figure 8:
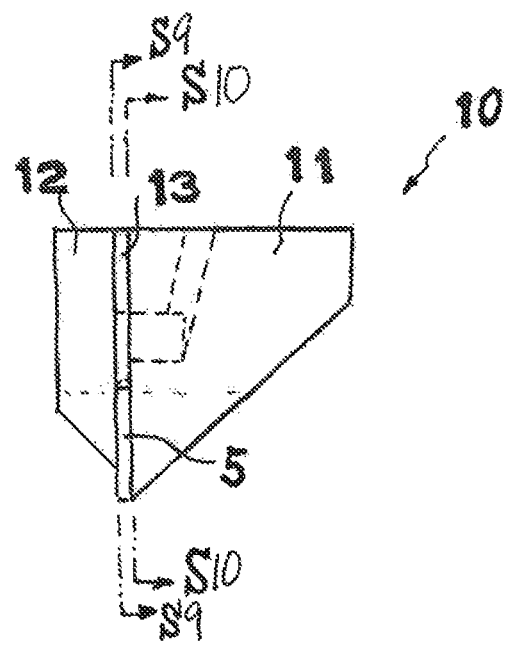
FIG. 8 is a side view of the same.
Figure 9:
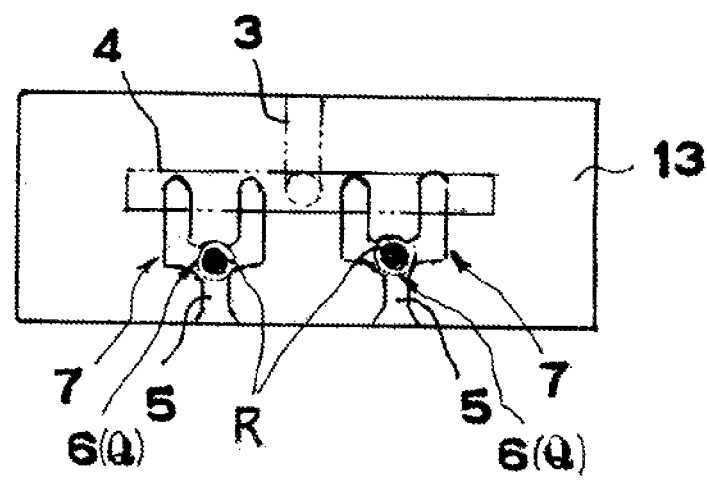
FIG. 9 is a longitudinal cross sectional view taken along the line S9-S9 in FIG. 8.
Figure 10:
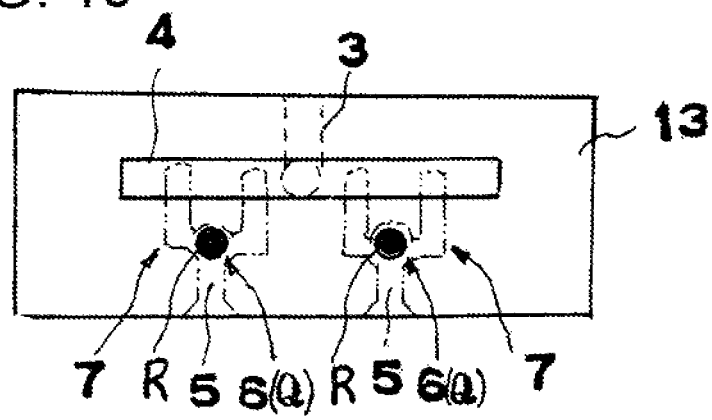
FIG. 10 is a longitudinal cross sectional view taken along the line S10-S10 in FIG. 8.
Figure 11A:
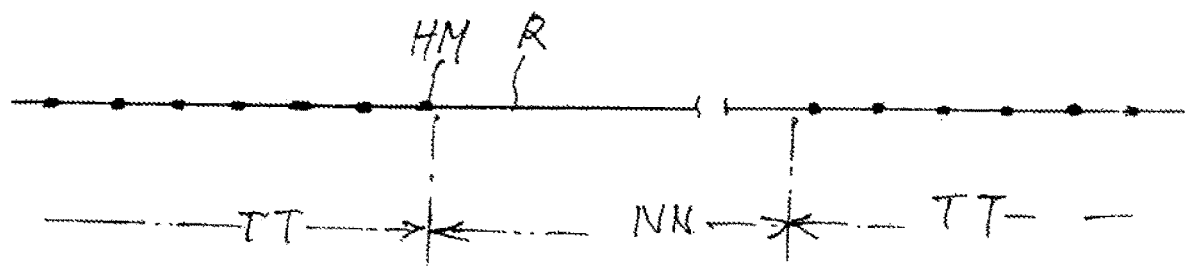
Figure 11B:
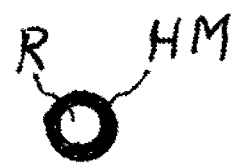

At the non-coating timing shown in FIG. 6, the protrusion 31 of the rotating body 30 is separated from the rubber threads R.

In this state, the rubber threads R are located below the coating area Q of the coating head 10. This is a non-coating state.

By selecting the number and spacing of the protrusions 31 of the rotating body 30, the pitch of the pleats can be adjusted to obtain optimum flexibility.

Referring to FIGS. 7 to 11, the coating head 10 is the same as a conventional device in that it is comprised of a head main body 11, a presser plate (blind plate) 12, and a shim plate (distribution plate) 13, an adhesive supply hole 3 and a distribution supply path 4 are formed in the head main body 11, and hot-melt adhesive is supplied to the adhesive application areas Q of slit grooves 5 of the shim plate 13 and in that the rubber threads, etc. R are supplied to and travel through the adhesive application areas Q of the slit grooves 5.

In working the present invention, communicating paths 7 are provided for supplying hot-melt adhesive to the left and right side portions of the adhesive application areas Q.

Each communicating path 7 is a left and right pair with respect to each slit groove 5. Also, the number of the slit grooves 5 (rubber threads R) may be one, two, four, or the like.

In regard to the communicating paths 7 with respect to their adjacent slit grooves 5, the upper end portion 7a on the inlet side may be shared, so that the lower end portions are branched off from the middle and that adhesive is supplied to an enlarged portion 6 of two slit grooves 5 through a single communicating path 7.

Figure 12A:
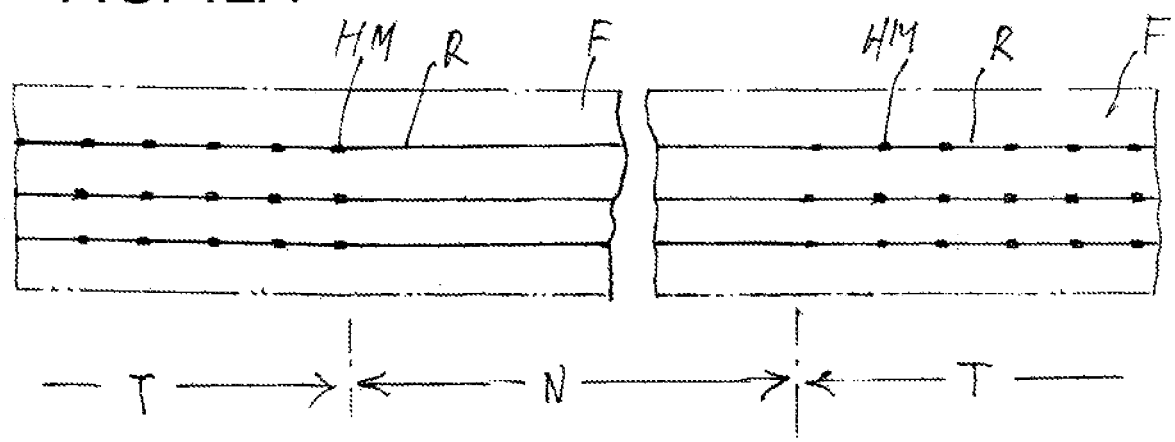
Figure 12B:
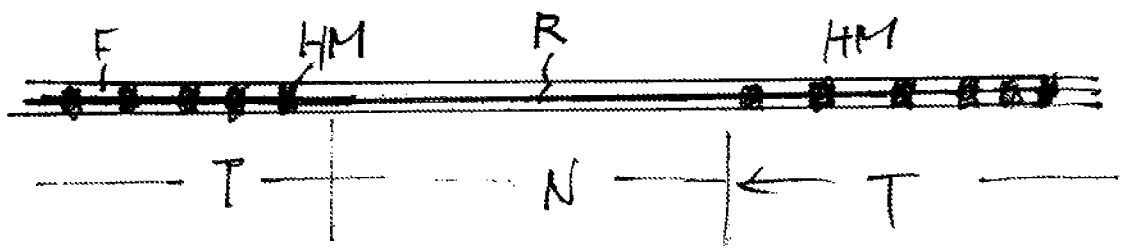

The steps for manufacturing a stretchable composite sheet will now be described. FIG. 12 shows the stretchable elastic members (rubber threads) R that are used, and it shows the extended state of stretchable elastic members (rubber threads) when the adhesive HM is applied to the entire peripheral surface of the stretchable elastic members (rubber threads) at specific hot-melt adhesive application positions.

In coating a plurality of stretchable elastic members (rubber threads) with a hot-melt adhesive, the non-continuous coating sections TT are set so as to correspond to a plurality of pleat formation regions T, and the non-coating sections NN are set corresponding to pleat-free regions N.

More specifically, in coating the stretchable elastic members (rubber threads) with the hot-melt adhesive, intermittent coating is performed to form the non-continuous coating sections TT and the non-coating sections NN.

At the adhesive application positions, the stretchable elastic members (rubber threads) to the entire peripheral surface of which the adhesive has adhered are supplied such that these adhesive application positions are at the contact points with the peaks of the pleats (folds).

Figure 13:
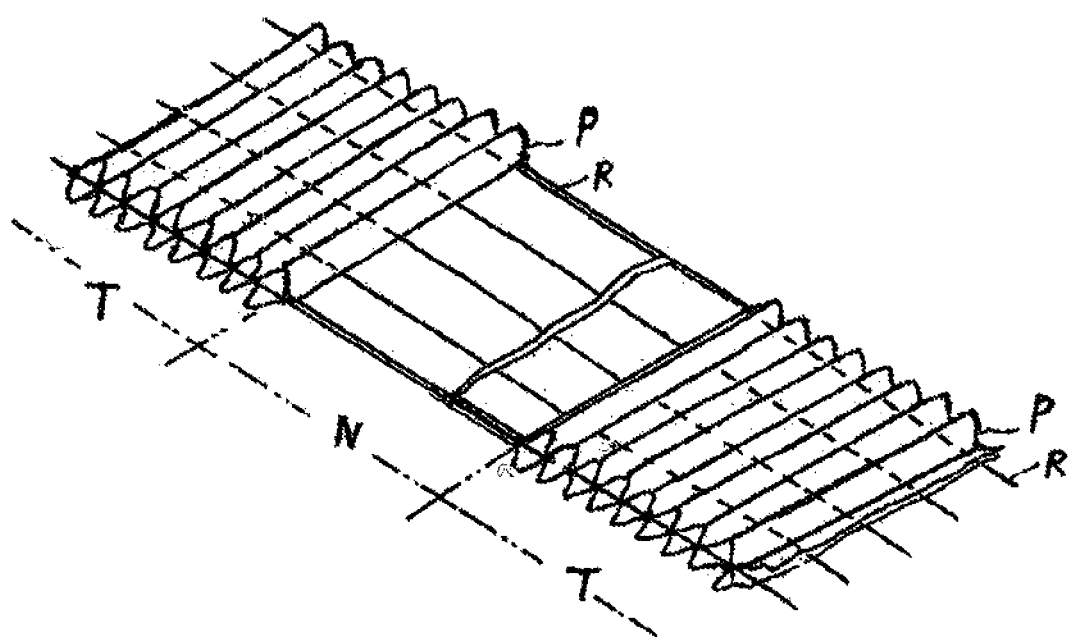
FIG. 13 is a perspective view of a stretchable composite sheet.

At an intermediate step of the stretchable composite sheet shown in FIG. 13, at the point when the entire peripheral surface of the stretchable elastic members (rubber threads) R is intermittently being coated with the hot-melt adhesive HM at specific intervals, the plurality of extended stretchable elastic members (rubber threads) R are disposed between two nonwoven fabric sheets F.

Thus, both sides of each of the plurality of stretchable elastic members (rubber threads) R are bonded and fixed to the nonwoven fabrics F at the contact points between the peaks of the two-layer pleats (folds) P and the plurality of stretchable elastic members (rubber threads) that are positioned orthogonally to the peaks of the pleats (folds).

Figure 14A:
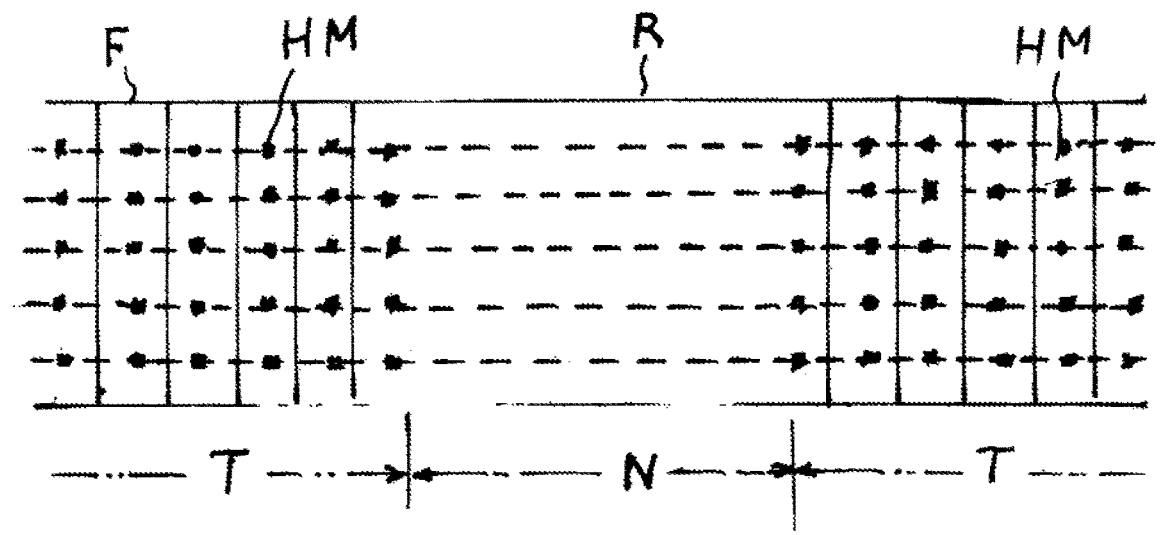
Figure 14B:
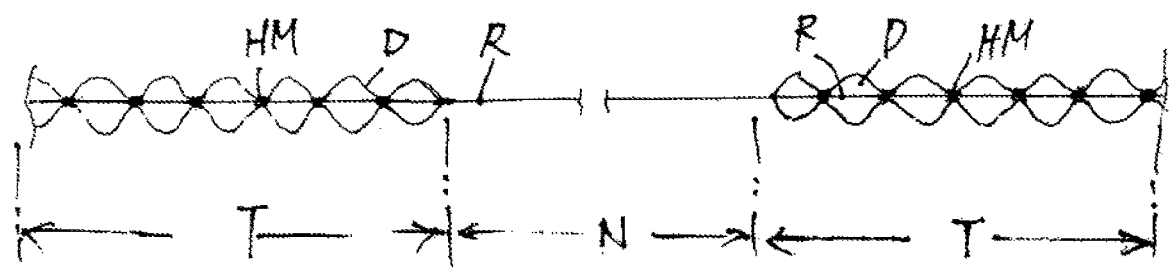
Figure 15:
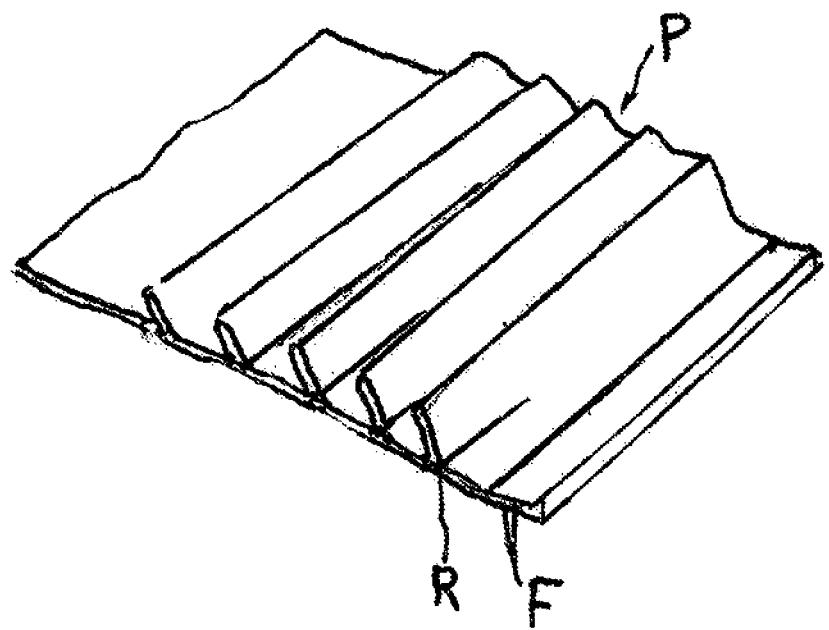
FIG. 15 is a perspective view of a stretchable composite sheet according to the third aspect of the invention of the present application.
Figure 16:
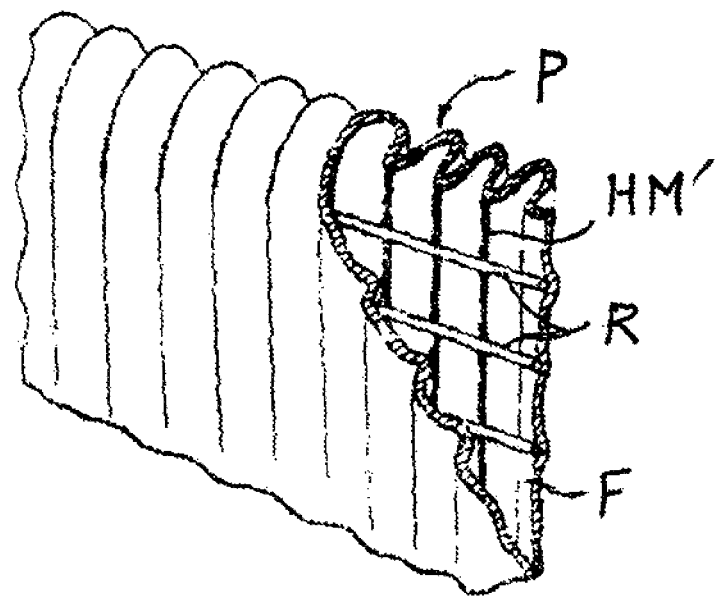
FIG. 16 is a perspective view of a known stretchable composite sheet disclosed in Patent Literature 1, which is partially cut away.
Figure 17:
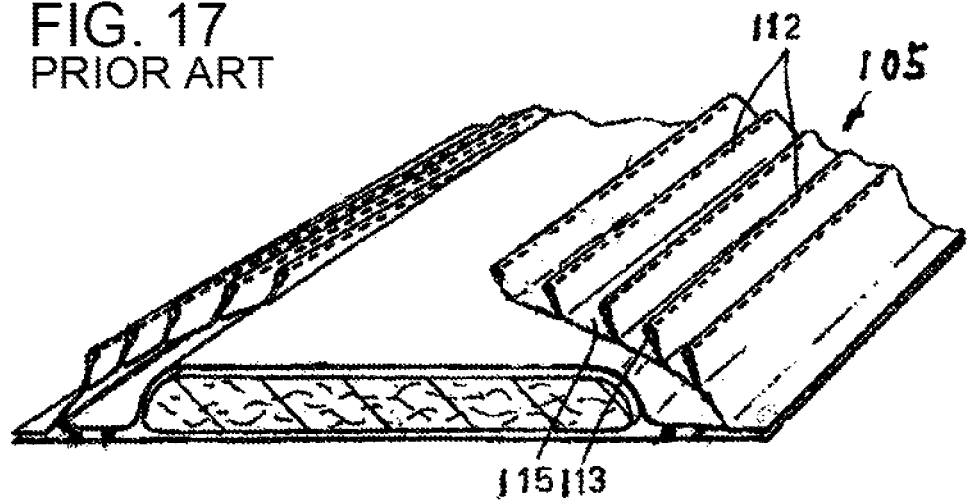
FIG. 17 is a perspective view of a known stretchable composite sheet disclosed in Patent Literature 2.

In an intermediate step for the stretchable composite sheet shown in FIGS. 14 and 15, at the adhesive application positions, the stretchable elastic members (rubber threads) to which entire peripheral surface the adhesive has adhered are supplied such that these adhesive application positions are at contact points with the peaks of the pleats (folds).

Both sides of the plurality of stretchable elastic members (rubber threads) are bonded and fixed to the nonwoven fabrics at contact points between the peaks of the two-layer pleats (folds) and the plurality of stretchable elastic members (rubber threads) that are positioned orthogonally to the peaks of the pleats (folds).

In a stretchable composite sheet in which a plurality of stretchable elastic members (rubber threads) are bonded and fixed between two nonwoven fabric sheets to form two-layer pleats <gathers> orthogonal to the plurality of stretchable elastic members (rubber threads), the stretchable composite sheet is completed in which pleats are formed such that both sides of the plurality of stretchable elastic members (rubber threads) are bonded and fixed to the nonwoven fabrics at the contact points between the peaks of the two-layer pleats <gathers> and the plurality of stretchable elastic members (rubber threads) that are positioned orthogonally to the peaks of the pleats <gathers>, and thus the plurality of pleat formation regions are formed, and pleat-free regions are formed where pleats are not formed between a plurality of the pleat formation regions.

The following reference matters are additionally described, although they do not limit the scope of the present invention. It is confirmed that the best pleats are formed in the embodiment under the following conditions:

Line speed of rubber threads R: 50 m/min
Non-continuous coating pitch: 7 mm

INDUSTRIAL APPLICABILITY

The present invention provides a stretchable composite member that is flexible, has a pleasant feel, and whose pleats are soft to the touch, for the manufacture of disposable diapers. Pleats that are optimal for absorbent products and the like can be formed, and the amount of adhesive that is applied can be reduced, thereby contributing to the development of fields of manufacture of disposable diapers and the like.

DESCRIPTION OF THE REFERENCE NUMERALS

P Pleat (fold)
R Stretchable elastic member (rubber thread)
1 Vertical drive device
10 Coating head
30 Rotating cam body

The invention claimed is:

1. An apparatus for applying an adhesive to stretchable members, comprising:
   a coating head that has slit grooves in which coating agent reservoirs are formed and is configured to apply an adhesive over an entire peripheral surface of rubber threads passing through the coating agent reservoirs; and
   a rubber thread vertical drive device that has slit grooves and is configured to move the rubber threads passing through the coating agent reservoirs up and down between a coating position at which the rubber threads pass through the coating agent reservoirs and a non-coating position at which the rubber threads pass away from the coating agent reservoirs,
   wherein the rubber thread vertical drive device is a rotating cam body that has a plurality of protrusions around a peripheral surface thereof and is driven synchronously with a feeding speed of the rubber threads.

2. The apparatus for applying an adhesive to stretchable members according to claim 1, wherein:
   a plurality of protrusions are formed on part of the peripheral surface of the rotating cam body that constitutes the rubber thread vertical drive device.

3. The apparatus for applying an adhesive to stretchable members according to claim 1, wherein:
   the rotating cam body that constitutes the rubber thread vertical drive device is formed with a protrusion section that has a plurality of continuous two protrusions on part of the peripheral surface and a flat section that has no protrusions.

\* \* \* \* \*